(12) United States Patent
Chen et al.

(10) Patent No.: US 12,661,120 B2
(45) Date of Patent: Jun. 23, 2026

(54) STAPLE CARTRIDGE, STAPLE CARTRIDGE ASSEMBLY, AND ANASTOMOSIS DEVICE

(71) Applicant: NINGBO VERYKIND MEDICAL DEVICE CO., LTD., Ningbo (CN)

(72) Inventors: Zaihong Chen, Ningbo (CN); Weiguo Fu, Ningbo (CN); Xin Yang, Ningbo (CN)

(73) Assignee: Ningbo Verykind Medical Device Co., Ltd., Ningbo (CN)

( * ) Notice: Subject to any disclaimer, the term of this patent is extended or adjusted under 35 U.S.C. 154(b) by 0 days.

(21) Appl. No.: 18/844,119

(22) PCT Filed: Jun. 12, 2024

(86) PCT No.: PCT/CN2024/098586
§ 371 (c)(1),
(2) Date: Sep. 5, 2024

(87) PCT Pub. No.: WO2025/251333
PCT Pub. Date: Dec. 11, 2025

(65) Prior Publication Data
US 2025/0375202 A1 Dec. 11, 2025

(30) Foreign Application Priority Data
Jun. 7, 2024 (CN) .......................... 202421299983.9

(51) Int. Cl.
*A61B 17/115* (2006.01)
*A61B 17/00* (2006.01)
*A61B 17/072* (2006.01)

(52) U.S. Cl.
CPC .... *A61B 17/1152* (2013.01); *A61B 17/07207* (2013.01); *A61B 2017/00477* (2013.01); *A61B 2017/07228* (2013.01); *A61B 2017/07271* (2013.01); *A61B 2017/07278* (2013.01)

(58) Field of Classification Search
CPC .... A61B 17/07207; A61B 2017/07214; A61B 2017/07228; A61B 2017/07271
See application file for complete search history.

(56) References Cited

U.S. PATENT DOCUMENTS

| | | | |
|---|---|---|---|
| 9,386,984 B2 * | 7/2016 | Aronhalt | .......... A61B 17/07292 |
| 11,707,275 B2 * | 7/2023 | Baril | .................... A61B 17/072 227/180.1 |
| 2004/0084505 A1 * | 5/2004 | Bilotti | .................. A61B 17/115 227/19 |
| 2006/0011699 A1 * | 1/2006 | Olson | .............. A61B 17/07207 227/19 |
| 2008/0023522 A1 * | 1/2008 | Olson | .................. A61B 17/105 227/175.1 |

(Continued)

*Primary Examiner* — Eronica Martin
*Assistant Examiner* — Mobeen Ahmed
(74) *Attorney, Agent, or Firm* — Troutman Pepper Locke LLP; Scott A. Bergeson; Aaron E. Johnston

(57) ABSTRACT

The present disclosure discloses a staple cartridge, a staple cartridge assembly, and an anastomosis device. A feeding groove of a staple cartridge provided in the present disclosure is arranged to extend in the first predetermined direction. Multiple staple slot groups are distributed on both sides of the feeding groove along the slot-width direction of the feeding groove, and the number of staple slot groups on both sides of the feeding groove is different.

15 Claims, 7 Drawing Sheets

(56) References Cited

U.S. PATENT DOCUMENTS

| | | | | | |
|---|---|---|---|---|---|
| 2011/0089221 A1* | 4/2011 | Masiakos | A61B 17/07207 | | |
| | | | 227/180.1 | | |
| 2011/0245578 A1* | 10/2011 | Wazer | A61N 5/1027 | | |
| | | | 600/3 | | |
| 2013/0056522 A1* | 3/2013 | Swensgard | A61B 17/07292 | | |
| | | | 227/176.1 | | |
| 2013/0248578 A1* | 9/2013 | Arteaga Gonzalez | | | |
| | | | A61B 17/068 | | |
| | | | 227/176.1 | | |
| 2013/0327808 A1* | 12/2013 | Chen | A61B 17/07207 | | |
| | | | 227/175.2 | | |
| 2014/0081176 A1* | 3/2014 | Hassan | A61B 90/06 | | |
| | | | 600/593 | | |
| 2014/0252065 A1* | 9/2014 | Hessler | A61B 17/0682 | | |
| | | | 227/176.1 | | |
| 2015/0108198 A1* | 4/2015 | Estrella | A61B 17/07207 | | |
| | | | 227/176.1 | | |
| 2015/0297235 A1* | 10/2015 | Harris | A61B 90/03 | | |
| | | | 227/176.1 | | |
| 2016/0157863 A1* | 6/2016 | Williams | A61B 17/068 | | |
| | | | 227/175.2 | | |
| 2016/0249929 A1* | 9/2016 | Cappola | A61B 17/07207 | | |
| | | | 227/176.1 | | |
| 2017/0172571 A1* | 6/2017 | Thompson | A61B 17/07207 | | |
| 2017/0189023 A1* | 7/2017 | Yan | A61B 17/07207 | | |
| 2017/0209145 A1* | 7/2017 | Swayze | A61B 17/07207 | | |
| 2017/0215880 A1* | 8/2017 | Davanzo Castillo | | | |
| | | | A61B 17/07207 | | |
| 2017/0281175 A1* | 10/2017 | Robinson | A61B 17/07207 | | |
| 2018/0168622 A1* | 6/2018 | Shelton, IV | A61B 17/07207 | | |
| 2019/0298354 A1* | 10/2019 | Shelton, IV | A61B 17/34 | | |
| 2020/0261081 A1* | 8/2020 | Boudreaux | A61B 50/00 | | |
| 2022/0079596 A1* | 3/2022 | Huitema | A61B 17/105 | | |
| 2022/0304690 A1* | 9/2022 | Baxter, III | A61B 17/07207 | | |
| 2022/0346787 A1* | 11/2022 | Shelton, IV | A61B 18/1445 | | |
| 2022/0409202 A1* | 12/2022 | Baril | A61B 17/07207 | | |
| 2023/0000491 A1* | 1/2023 | Wise | A61B 34/30 | | |
| 2023/0045893 A1* | 2/2023 | Shelton, IV | A61B 34/76 | | |
| 2023/0050358 A1* | 2/2023 | Shelton, IV | A61B 17/0686 | | |
| 2023/0050707 A1* | 2/2023 | Shelton, IV | A61B 17/07207 | | |
| 2023/0051361 A1* | 2/2023 | Shelton, IV | A61B 34/00 | | |
| 2023/0404576 A1* | 12/2023 | Whitfield | A61B 17/07207 | | |
| 2024/0252159 A1* | 8/2024 | Schmid | A61B 17/072 | | |
| 2024/0350137 A1* | 10/2024 | Fanelli | A61B 17/07207 | | |
| 2025/0120700 A1* | 4/2025 | Fiebig | A61B 17/07207 | | |
| 2025/0120702 A1* | 4/2025 | Shelton, IV | A61B 17/07207 | | |
| 2025/0120704 A1* | 4/2025 | Shelton, IV | A61B 17/07207 | | |
| 2025/0120714 A1* | 4/2025 | Shelton, IV | A61B 17/07207 | | |
| 2025/0318830 A1* | 10/2025 | Choi | A61B 17/07207 | | |
| 2025/0325266 A1* | 10/2025 | Baril | A61B 17/07207 | | |

* cited by examiner

STAPLE CARTRIDGE, STAPLE CARTRIDGE ASSEMBLY, AND ANASTOMOSIS DEVICE

CROSS-REFERENCE TO RELATED APPLICATION

This application is a National Stage Entry of, and claims priority to, PCT Patent Application No. PCT/CN2024/098586 filed on Jun. 12, 2024, which claims the priority to the Chinese patent application with the filling No. 202421299983.9 filed with the Chinese Patent Office on Jun. 7, 2024, and entitled "STAPLE CARTRIDGE, STAPLE CARTRIDGE ASSEMBLY, AND ANASTOMOSIS DEVICE", the contents of which are incorporated herein by reference in entirety.

TECHNICAL FIELD

The present disclosure relates to the technical field of medical devices, and particularly to a staple cartridge, a staple cartridge assembly, and an anastomosis device.

BACKGROUND ART

The anastomosis device (stapler) is a medical instrument commonly used in surgical operations to anastomose tissues. The anastomosis device includes components such as a staple cartridge assembly and a staple-abutting seat. During surgery, the cutting knife drives the staple-pushing member to move, and the staple-pushing movement of the staple-pushing member triggers the anastomotic staple in the staple cartridge of the staple cartridge assembly. The triggered anastomotic staples pierce the tissue and deform when interacting with the staple-abutting seat, thereby completing the anastomosis operation. Simultaneously, the cutting knife completes the cutting operation. Typically, the two sides of the path of the cutting knife correspond to the tissue retention end and the tissue removal end, respectively, and both the tissue retention end and the tissue removal end undergo anastomosis operations with the anastomotic staples.

However, when performing anastomosis operations using an anastomosis device in the prior art, it is easy to encounter problems of poor anastomosis effect and excessive bleeding at the tissue retention end, while an over-functioning anastomosis is present at the tissue removal end.

SUMMARY

In view of this, the objective of the present disclosure includes providing a staple cartridge, a staple cartridge assembly, and an anastomosis device, thereby aiming to improve the problems in the prior art where the anastomosis device leads to poor anastomosis effect and excessive bleeding at the tissue retention end, and the over-functioning anastomosis at the tissue removal end.

In order to achieve the above objective, the technical solution applied in the present disclosure is as follows.

In a first aspect, the embodiments of the present disclosure provide a staple cartridge, wherein the staple cartridge is provided with a feeding groove and multiple staple slot groups. The feeding groove is arranged to extend in a first predetermined direction, and the feeding groove is configured for the passage of a cutting knife. Each of the staple slot groups includes multiple staple slots distributed along the first predetermined direction, wherein the staple slots are configured for mounting the anastomotic staples. The multiple staple slot groups are arranged at intervals in a slot-width direction of the feeding groove. At least one staple slot group is distributed on both sides of the feeding groove in the slot-width direction, and the number of staple slot groups on both sides of the feeding groove in the slot-width direction is different.

In an optional embodiment, the feeding groove is arranged to extend in a straight line, wherein one end of the feeding groove is provided with a first open port. The first open port is configured for the cutting knife to enter the feeding groove along the first predetermined direction.

In an optional embodiment, the multiple staple slot groups on the same side of the feeding groove are distributed at equal intervals.

In an optional embodiment, the staple slots of two adjacent staple slot groups on the same side of the feeding groove are distributed in a staggered manner.

In an optional embodiment, two or more staple slot groups are provided on either side of the feeding groove in the slot-width direction.

In an optional embodiment, the difference in the number of staple slot groups on both sides of the feeding groove in the slot-width direction is less than or equal to two.

In an optional embodiment, the feeding groove and the staple slots penetrate the staple cartridge along a second predetermined direction, wherein the second predetermined direction is perpendicular to the first predetermined direction and the slot-width direction. The staple cartridge is provided with a first side and a second side that are opposite in the second predetermined direction. The opening of the staple slot formed on the first side of the staple cartridge is configured for the front end of the triggered anastomotic staple to extend out, and the second side of the staple cartridge is provided with multiple staple-pushing slots extending in the first predetermined direction. The staple-pushing slots are arranged between two adjacent staple slot groups on the same side of the feeding groove. The staple-pushing slots communicate with the staple slots of two adjacent staple slot groups in the slot-width direction. The staple-pushing slot is configured to allow at least a portion of the staple-pushing member to pass through, so as to push the anastomotic staples located in the staple slots toward the first side of the staple cartridge.

In an optional embodiment, one end of the staple-pushing slot is provided with a second open port, wherein the second open port is configured for the staple-pushing member to pass through along the first predetermined direction.

In an optional embodiment, the second side of the staple cartridge is provided with a guide slot extending in the first predetermined direction, wherein the guide slot is configured to be in a sliding fit with the guide part of the staple-pushing member.

In a second aspect, the embodiments of the present disclosure provide a staple cartridge assembly, including a staple-pushing member and any one of the staple cartridges in the first aspect mentioned above, wherein the staple-pushing member is configured to move relative to the staple cartridge so as to trigger the anastomotic staples in the staple slots of the staple cartridge.

In an optional embodiment, the feeding groove and the staple slots penetrate the staple cartridge along a second predetermined direction, wherein the second predetermined direction is perpendicular to the first predetermined direction and the slot-width direction. The staple cartridge is provided with a first side and a second side that are opposite in the second predetermined direction. The opening of the staple slot formed on the first side of the staple cartridge is configured for the front end of the triggered anastomotic staple to extend out, and the second side of the staple cartridge is provided with multiple staple-pushing slots extending in the first predetermined direction. The staple-pushing slots are arranged between two adjacent staple slot groups on the same side of the feeding groove. The staple-pushing slots communicate with the staple slots of two adjacent staple slot groups in the slot-width direction.

The staple-pushing member is arranged on the second side of the staple cartridge. At least a portion of the staple-pushing member extends into the staple-pushing slot and can move along the staple-pushing slot, so as to push the anastomotic staples located in the staple slots to move toward the first side of the staple cartridge.

In an optional embodiment, the staple-pushing member includes multiple staple-pushing plates, wherein the multiple staple-pushing plates are arranged at intervals in the slot-width direction. The staple-pushing plates and the staple-pushing slots are provided in same number and inserted into the staple-pushing slots in a one-to-one correspondence.

In an optional embodiment, one end of the staple-pushing plate in the first predetermined direction is provided with a guide surface, wherein the guide surface is inclined relative to the first predetermined direction and inclined towards the second side of the staple cartridge. The guide surface is configured to push the anastomotic staples toward the first side of the staple cartridge when moving along the first predetermined direction.

In an optional embodiment, the second side of the staple cartridge is provided with a guide slot extending in the first predetermined direction. The staple-pushing member further includes a guide part, wherein the guide slot is in a sliding fit with the guide part of the staple-pushing member.

In an optional embodiment, the staple cartridge assembly further includes a staple seat and the anastomotic staples, wherein the staple seat is housed in the staple slot and the staple-pushing slot. The staple seat includes two connected sub staple seats, wherein the two sub staple seats are respectively in sliding fit with the staple slots in the two adjacent staple slot groups so that the staple seat can move relative to the staple cartridge in the second predetermined direction. Each sub staple seat is provided with one anastomotic staple at an end near the first side of the staple cartridge.

In an optional embodiment, the staple-pushing member is configured to move relative to the staple cartridge in the first predetermined direction. The staple cartridge assembly further includes an elastic limiting unit and the staple cartridge is provided with a mounting hole, wherein the elastic limiting unit is mounted at the mounting hole. The elastic limiting unit includes an elastic force transfer structure and a trigger part and a limiting part located at both ends of the elastic force transfer structure, wherein the trigger part and the limiting part are respectively arranged near an inner end and an outer end of the mounting hole. The trigger part is arranged in a pushing movement path of the staple-pushing member in the first predetermined direction. The elastic limiting unit is configured to produce an elastic deformation when the trigger part is pushed by the staple-pushing member so that the trigger part exits the pushing movement path. The elastic force transfer structure is configured to apply an elastic driving force to the limiting part for extending towards the outer end of the mounting hole when the trigger part exits the pushing movement path.

In an optional embodiment, the staple cartridge is provided with the trigger part corresponding to a terminal limiting position of the pushing movement path of the staple-pushing member;

and/or the elastic limiting unit is an elastic piece structure, wherein a fixed end of the elastic piece structure is fixedly arranged at an edge of the mounting hole, and the elastic force transfer structure, the trigger part, and the limiting part are all formed on the elastic piece structure.

In an optional embodiment, the elastic piece structure is bent to form a first section, a second section, and a third section sequentially connected, wherein the first section forms the fixed end of the elastic piece structure and is fixedly connected to the staple cartridge, and the second section and the third section are each provided in an inclined manner with respect to the first section. The third section and the second section form an angle, and the opening direction of the angle formed by the second section and the third section is consistent with the depth direction of the mounting hole. The connection part of the second section and the third section forms the trigger part, and the third section forms the elastic force transfer structure.

In an optional embodiment, the staple cartridge assembly further includes a staple cartridge cover, wherein the staple cartridge cover is detachably connected to the staple cartridge. The staple cartridge cover forms a holding space, wherein the staple cartridge is arranged in the holding space of the staple cartridge cover. The staple cartridge cover is provided with a through hole, wherein the through hole communicates with the mounting hole, and the through hole is configured for the limiting part to pass through. The inner wall of the staple cartridge cover and the outer wall of the staple cartridge clamp the fixed end of the elastic piece structure.

In the third aspect, the embodiments of the present disclosure provide an anastomosis device, including any of the staple cartridge assemblies in the second aspect mentioned above.

The beneficial effects of the present disclosure are the following.

Compared to the related prior art, in the staple cartridge, staple cartridge assembly, and anastomosis device of the present disclosure, the feeding groove of the staple cartridge is arranged to extend in a first predetermined direction, wherein the feeding groove is configured for the cutting knife to pass through. When the staple cartridge is applied to the anastomosis device, specifically, when the anastomosis device compresses the tissue to be operated on through the staple-abutting seat and the staple cartridge, the cutting knife can perform cutting operations by moving through the feeding groove. At the same time, multiple staple slot groups are distributed on both sides of the feeding groove along the slot-width direction of the feeding groove, and the number of staple slot groups on both sides of the feeding groove is different, thereby making the stability of the anastomosis and the width of the anastomosis on both sides of the feeding groove different along the slot-width direction. This can specifically enhance the stability of the anastomosis on the side with a greater number of staple slot groups and can meet the differentiated anastomotic requirements of the tissue retention end and the tissue removal end. Specifically, the side with a greater number of staple slot groups corresponds to the tissue retention end, and the side with fewer staple slot groups corresponds to the tissue removal end, which can meet the anastomotic requirements of the tissue retention end, improve the anastomosis effect on the tissue retention end, and reduce the amount of bleeding on the tissue retention end. Simultaneously, it can also prevent over-functioning anastomosis on the tissue removal end due to too many anastomotic staples, thus avoiding the waste of anastomotic staples. Overall, the staple cartridge in the embodiments of the present disclosure is beneficial for improving the utilization rate of anastomotic staples, reducing the amount of bleeding on the tissue retention end, and enhancing the anastomosis effect on the tissue retention end.

BRIEF DESCRIPTION OF DRAWINGS

To more clearly illustrate the technical solutions of the embodiments of the present disclosure, the following will briefly introduce the drawings used in the embodiments. It should be understood that the following drawings only show some embodiments of the present disclosure, and therefore they should not be regarded as a limitation on the scope. Those ordinary skilled in the art can also obtain other related drawings based on these drawings without inventive effort.

REFERENCE NUMERALS

Figure 1:
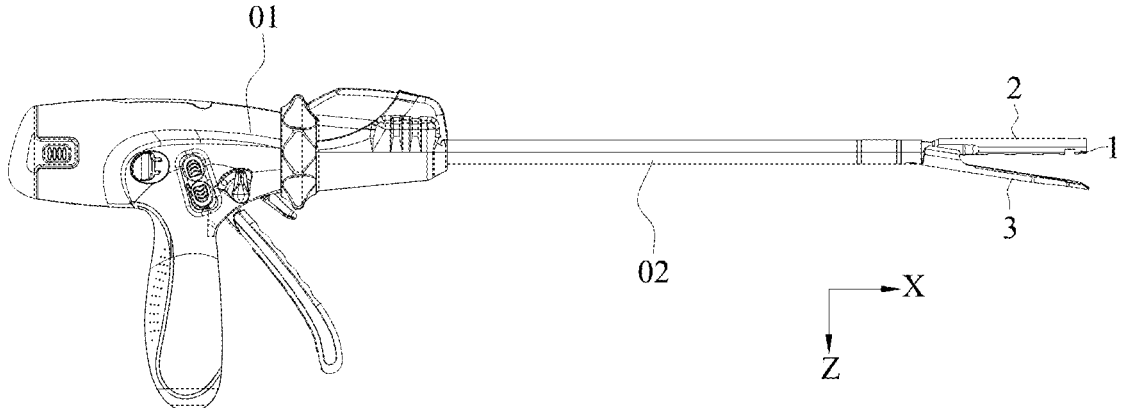
FIG. 1 is a schematic diagram of an anastomosis device in one embodiment of the present disclosure.

1—staple cartridge assembly; 11—staple cartridge; 111—mounting hole; 112—first side wall; 113—feeding groove; 1131—first open port; 114—staple slot group; 1141—staple slot; 115 slot; 116—staple-pushing slot; 1161—second open port; 117—guide slot; 12—elastic limiting unit; 121—trigger part; 122—limiting part; 123—elastic force transfer structure; 12a—first section; 12b—second section; 12c—third section; 12d—insertion section; 13—staple-pushing member; 131—staple-pushing plate; 1311—guide surface; 132—guide part; 14—staple cartridge cover; 141—through hole; 15—staple seat; 151—sub staple seat; 16—protective member; 161—snapping part; 2—staple cartridge base; 21—slot structure; 3—staple-abutting seat; 31—forming slot; 311—groove; 4—anastomotic staple.

DETAILED DESCRIPTION OF EMBODIMENTS

The following describes the embodiments of the present disclosure in detail. Examples of the embodiments are illustrated in the drawings, where the same or similar reference numerals throughout indicate the same or similar elements or elements having the same or similar functions. The embodiments described below by reference to the drawings are exemplary and are intended only to explain the present disclosure and are not to be construed as a limitation of the present disclosure.

In the description of the present disclosure, it is to be understood that the terms, such as "center", "longitudinal", "lateral", "length", "width", "thickness", "up", "down", "front", "back", "left", "right", "vertical", "horizontal", "top", "bottom", "inside", "outer", "clockwise", "counter-clockwise", "axial", "radial", and "circumferential" indicate orientations or positional relationships based on those shown in the drawings, and are intended only to facilitate the description of the present disclosure and to simplify the description, and are not intended to indicate or imply that the device or element referred to must have a particular orientation, be constructed and operated in a particular orientation, and therefore cannot be construed as a limitation of the present disclosure.

Additionally, the terms "first" and "second" are used for descriptive objectives only and should not be understood as indicating or implying relative importance or specifying the quantity of the indicated technical features. Consequently, features labeled with "first" or "second" can explicitly or implicitly include one or more of those features. In the description of the present disclosure, the term "multiple" means two or more, unless otherwise explicitly specified.

In the present disclosure, unless otherwise expressly provided and limited, the first feature "on" or "under" the second feature may be a direct contact between the first and second features, or an indirect contact between the first and second features through an intermediate medium. Furthermore, the first feature being "above", "over", and "on top of" the second feature can mean that the first feature is directly above or diagonally above the second feature, or simply that the first feature is horizontally higher than the second feature. The first feature being "under", "below" and "beneath" the second feature can mean that the first feature is directly below or diagonally below the second feature, or it can simply mean that the horizontal height of the first feature is less than that of the second feature.

In the staple cartridge assembly of the anastomosis device of the related art, the number of anastomotic staples on both sides of the path of the cutting knife is designed to be the same. Therefore, the anastomosis widths of the tissue retention end and the tissue removal end being anastomosed by the anastomotic staple are the same when using the anastomosis device in the related art for tissue anastomosis operations. However, the inventors have found that the tissue retention end and the tissue removal end have different requirements for the degree of anastomosis. When using the anastomosis device of the related art, the tissue retention end can suffer from significant bleeding due to an insufficient number of anastomotic staples, which affects the anastomosis results. However, the tissue removal end can suffer from over-functioning anastomosis and the wastage of anastomotic staples due to an excessive number of anastomotic staples.

To address at least one of the above-mentioned deficiencies in the related art, the embodiments of the present disclosure provide a staple cartridge, a staple cartridge assembly, and an anastomosis device. By distributing different numbers of staple slots on both sides of the feeding groove on the staple cartridge, a different number of anastomotic staples can be configured, which meets the differentiated needs for the degree of anastomosis required by the tissue removal end and the tissue retention end, enhances the anastomosis effect, and reduces the wastage of anastomotic staples.

The staple cartridge, the staple cartridge assembly, and the anastomosis device provided by the embodiments of the present disclosure are described below in conjunction with the drawings. In the drawings, the Z-axis represents the vertical direction, i.e., the up and down positions, with the positive direction of the Z-axis (i.e., the direction of the arrow in the Z-axis) indicating up, and the negative direction of the Z-axis indicating down. The X-axis represents the front and back positions, with the positive direction of the X-axis (i.e., the direction of the arrow in the X-axis) indicating the front, and the negative direction of the X-axis indicating the back. The Y-axis represents the horizontal direction, specified as the left and right positions, with the positive direction of the Y-axis (i.e., the direction of the arrow in the Y-axis) indicating the right, and the negative direction of the Y-axis indicating the left. It should be noted that the meanings of the Z-axis, the Y-axis, and the X-axis are provided merely for the convenience of describing the present disclosure and for simplifying the description, and are not intended to indicate or imply that the referenced devices or elements must have specific orientations or operate in specific orientations. Therefore, they should not be construed as limiting the present disclosure.

FIG. 1 is a schematic diagram of an anastomosis device in one embodiment of the present disclosure. As shown in FIG. 1, the anastomosis device provided by the embodiment of the present disclosure includes a drive body 01, a transmission assembly 02, a cutting knife (not shown in the figure), a staple cartridge base 2, a staple-abutting seat 3, and a staple cartridge assembly 1. The transmission assembly 02 is connected between the staple cartridge assembly 1 and the drive body 01. The drive body 01 provides driving force, and the transmission assembly 02 transmits the momentum to the cutting knife, which can allow the cutting knife and the staple-pushing member 13 in the staple cartridge assembly 1 to slide synchronously within the staple cartridge assembly 1. Therefore, the operations of cutting and anastomosing on tissues are achieved. In the embodiment shown in FIG. 1, the staple cartridge base 2, the staple-abutting seat 3, and the staple cartridge assembly 1 are all located at the front end of the anastomosis device. The anastomosis device can be used in laparoscopic surgeries and other procedures, such as the removal of diseased tissue, without being limited to these applications.

Figure 2:
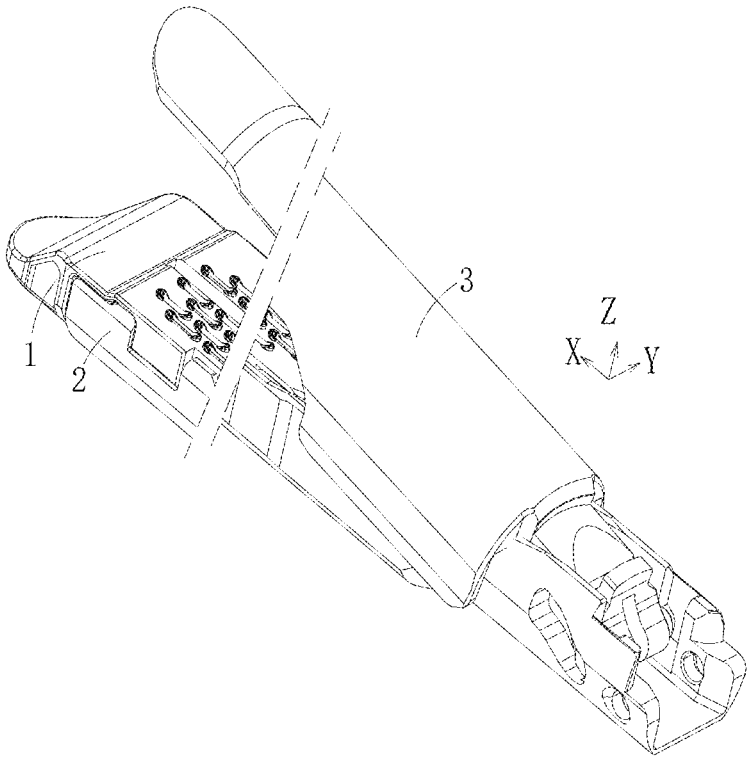
FIG. 2 is a schematic diagram of an assembly of a staple cartridge base, a staple cartridge assembly, and a staple-abutting seat in one embodiment of the present disclosure.
Figure 3:
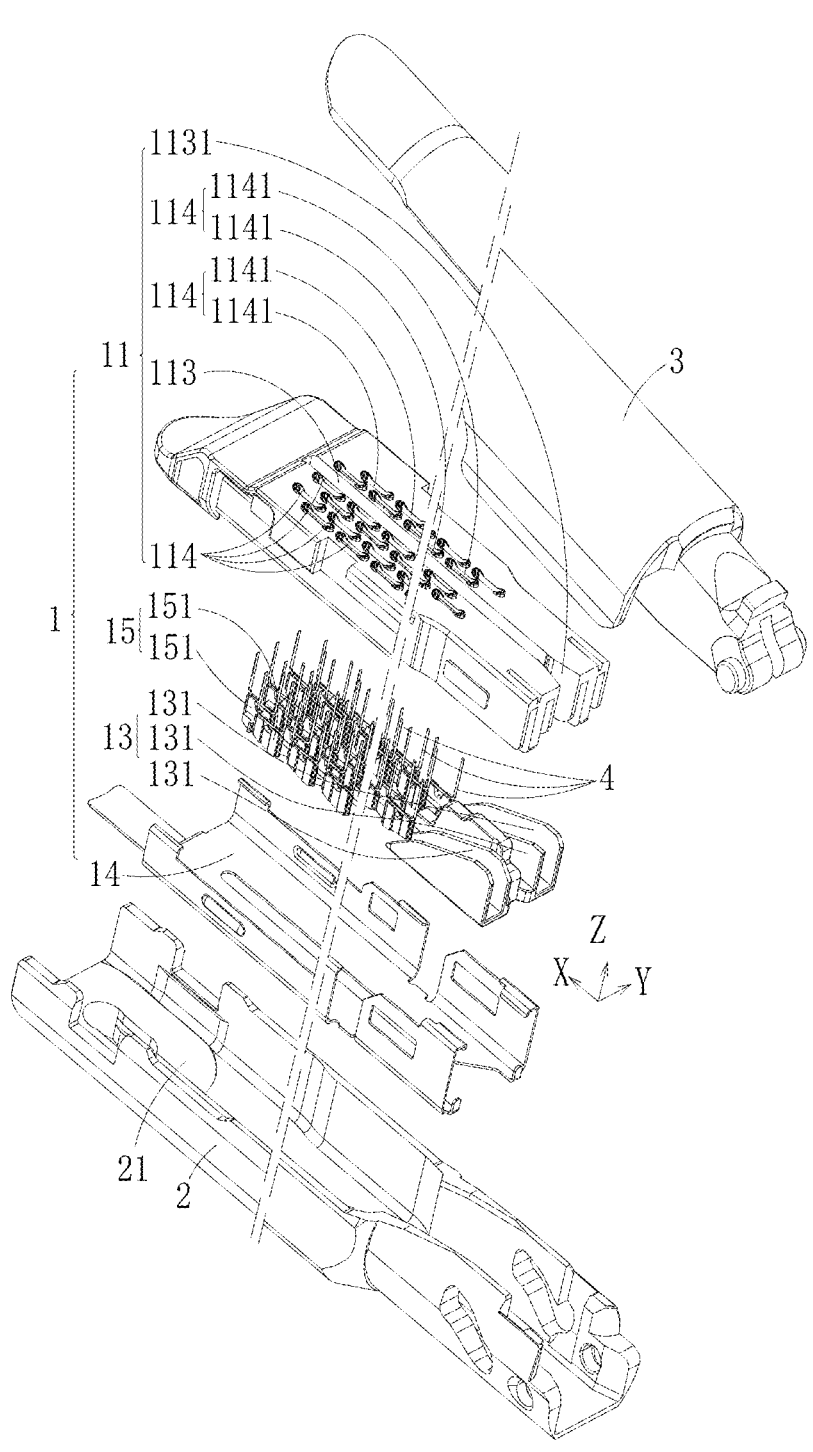
FIG. 3 is an exploded schematic diagram of the staple cartridge base, the staple cartridge assembly, and the staple-abutting seat in one embodiment of the present disclosure.

FIG. 2 is a schematic diagram of an assembly of a staple cartridge base, a staple cartridge assembly, and a staple-abutting seat in one embodiment of the present disclosure. FIG. 3 is an exploded schematic diagram of the staple cartridge base, the staple cartridge assembly, and the staple-abutting seat in one embodiment of the present disclosure. As shown in FIGS. 2 and 3, in the embodiment, the staple cartridge base 2 is configured to fixedly mount the staple cartridge assembly 1. The staple-abutting seat 3 is configured to clamp the tissue to be anastomosed together with the staple cartridge assembly 1 and is also configured to abut against the anastomotic staples 4 triggered from the staple cartridge assembly 1, thus deforming the anastomotic staples 4 to enable anastomosis operation on the tissue. Optionally, the staple-abutting seat 3 is connected to one end of the staple cartridge base 2 in a rotating manner, allowing the staple-abutting seat 3 and the staple cartridge base 2 to open and close in a manner of relative motion.

The staple cartridge assembly 1 provided by the embodiments of the present disclosure includes a staple cartridge 11, a staple-pushing member 13, a staple seat 15, and anastomotic staples 4. The anastomotic staples 4 are mounted on the staple seat 15, and the staple cartridge 11 is configured to house the staple seat 15 and the anastomotic staples 4 before the anastomosis operation. The staple-pushing member 13 is configured to move relative to the staple cartridge 11 under the drive of the drive body 01 so as to trigger the anastomotic staples 4 out of the staple cartridge 11 and implant into the tissue, thereby achieving the anastomosis operation.

In the embodiments of the present disclosure, the staple cartridge 11 is provided with a feeding groove 113 and multiple staple slot groups 114. The feeding groove 113 is arranged to extend along the first predetermined direction, which is parallel to the extending direction of the X-axis in the figure. The feeding groove 113 is configured to allow the cutting knife to pass through. When the staple cartridge 11 is in use, the cutting knife can smoothly pass through the feeding groove 113, thereby completing the cutting operation.

Multiple staple slot groups 114 are distributed along the slot-width direction of the feeding groove 113, which is parallel to the Y-axis direction in the figure. At least one staple slot group 114 is distributed on both sides of the feeding groove 133 in the slot-width direction, and the numbers of staple slot groups 114 on both sides of the feeding groove 113 are different. Each staple slot group 114 includes multiple staple slots 1141 distributed along the first predetermined direction. In other words, a staple slot group 114 consists of a row of staple slots 1141 arranged along the first predetermined direction. The staple slots 1141 are configured to mount the anastomotic staples 4. The anastomotic staples 4 are triggered by the movement of the staple-pushing member 13, which will be exemplarily described later.

Since the feeding groove 113 of the staple cartridge 11 is arranged to extend in the first predetermined direction, the feeding groove 113 can limit the movement of the cutting knife along the first predetermined direction. During the operation, the anastomosis device compresses the tissue to be operated on through the staple-abutting seat 3 and the staple cartridge 11, the cutting knife can perform cutting operations by moving through the feeding groove 113. At the same time, multiple staple slot groups 114 are distributed on both sides of the feeding groove 113 along the slot-width direction of the feeding groove 113, and the number of staple slot groups 114 on both sides of the feeding groove 113 is different so that the stability of the anastomosis and the width of the anastomosis on both sides of the feeding groove 113 along the slot-width direction are different. This can specifically enhance the stability of the anastomosis on the side with a greater number of staple slot groups 114 and can meet the differentiated anastomotic requirements of the tissue retention end and the tissue removal end. Specifically, the side with a greater number of staple slot groups 114 corresponds to the tissue retention end, and the side with fewer staple slot groups 114 corresponds to the tissue removal end, which can meet the anastomotic requirements of the tissue retention end, reduce the amount of bleeding on the tissue retention end, and improve the anastomosis effect on the tissue retention end. It can also address the problems of the over-functioning anastomosis and the wastage of anastomotic staples 4 on the tissue removal end due to too many anastomotic staples 4. Overall, the embodiments of the present disclosure are beneficial for improving the utilization rate of anastomotic staples 4, reducing the amount of bleeding on the tissue retention end, and enhancing the anastomosis effect on the tissue retention end.

As shown in FIG. 3, optionally, the feeding groove 113 is arranged to extend in a straight line, wherein one end of the feeding groove 113 is provided with a first open port 1131 for the cutting knife to pass through. Specifically, the first open port 1131 is located at the rear end of the feeding groove 113, that is, the end towards the negative direction of the X-axis in the figure. With this arrangement, the cutting knife can enter the feeding groove 113 through the first open port 1131 along the first predetermined direction and move in a straight line along the first predetermined direction to perform the cutting action. Therefore, the staple cartridge 11 of the embodiment can be applied to linear anastomosis devices, which can anastomose along the straight-line direction, with simple structure and high practicality.

As shown in FIG. 3, optionally, two or more staple slot groups 114 are provided on either side of the feeding groove 113 along the slot-width direction. In other words, the number of staple slot groups 114 on both the left side and right side of the feeding groove 113 is greater than two. Optionally, three staple slot groups 114 are provided on the left side, and two staple slot groups 114 are provided on the right side, in which this solution is not shown in the figure. With this arrangement, it is possible to avoid providing too few staple slot groups 114 on both sides of the feeding groove 113, which affects the anastomosis effect at the corresponding positions.

Optionally, the difference in the number of staple slot groups 114 on both sides of the feeding groove 113 along the slot-width direction is less than or equal to two. For example, if the number of staple slot groups 114 on the left side of the feeding groove 113 is greater than the number of staple slot groups 114 on the right side of the feeding groove 113, the difference between the number of staple slot groups 114 on the left side and the number of staple slot groups 114 on the right side is one or two.

As shown in FIG. 3, optionally, the left side of the feeding groove 113 is provided with four staple slot groups 114, and the right side of the feeding groove 113 is provided with two staple slot groups 114. In other optional embodiments, the left side of the feeding groove 113 is provided with three staple slot groups 114, and the right side of the feeding groove 113 is provided with two staple slot groups 114, in which this solution is not shown in the figure.

This arrangement can prevent the difference in the number of staple slot groups 114 on the two sides of the feeding groove 113 from being too large, which could cause the total size of the staple cartridge 11 along the slot-width direction of the feeding groove 113 to be too large, thereby affecting the applicability of the anastomosis device.

It should be understood that the relative location relationship of multiple staple slot groups 114 along the slot-width direction of the feeding groove 113, i.e., the Y-axis direction in the figure, can be set according to actual needs. Optionally, multiple staple slot groups 114 on the same side of the feeding groove 113 are distributed at equal intervals. Optionally, the staple slot 1141 of two adjacent staple slot groups 114 are distributed in a staggered manner so that the anastomosed anastomotic staples 4 are arranged in multiple rows along the Y-axis direction, and, the anastomotic staples 4 of two adjacent rows on the same side are distributed in a staggered manner, which can ensure the stapling effect.

Figure 4:
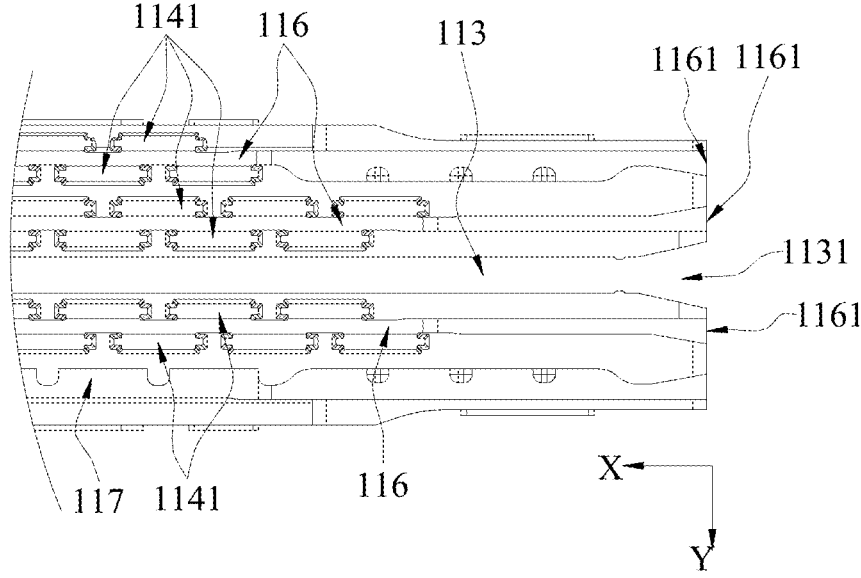
FIG. 4 is a partially schematic diagram of a second side of the staple cartridge in one embodiment of the present disclosure.

FIG. 4 is a partial schematic diagram of a second side of the staple cartridge in one embodiment of the present disclosure. As shown in FIG. 4, the feeding groove 113 and the staple slots 114 penetrate the staple cartridge along the second predetermined direction, which is parallel to the Z-axis direction in the figure. The second predetermined direction is perpendicular to the first predetermined direction and the slot-width direction. The staple cartridge 11 is provided with a first side and a second side in the second predetermined direction, where FIG. 2 and FIG. 3 show the first side of the staple cartridge 11, and FIG. 4 shows the second side of the staple cartridge 11. The opening of the staple slot 1141 formed on the first side of the staple cartridge 11 is configured for the front end of the triggered anastomotic staple 4 to extend. The second side of the staple cartridge 11 is provided with multiple staple-pushing slots 116 extending in the first predetermined direction, wherein the staple-pushing slots 116 are arranged between two adjacent staple slot groups 114 on the same side of the feeding groove 113, and the staple-pushing slots 116 communicate with the staple slots 1141 of two adjacent staple slot groups 114 in the slot-width direction. The staple-pushing member 13 is arranged on the second side of the staple cartridge 11, and the staple-pushing member 13 is configured to move relative to the staple cartridge 11 in the first predetermined direction. At least a portion of the staple-pushing member 13 extends into the staple-pushing slot 116 and can move along the staple-pushing slot 116, so as to push the anastomotic staples 4 located in the staple slots 1141 to move toward the first side of the staple cartridge 11. The staple-pushing slot 116 is configured to allow at least a portion of the staple-pushing member 13 to pass through so that the anastomotic staples 4 in the staple slots 1141 can be pushed by the staple-pushing member 13 to move towards the first side of the staple cartridge 11. It can be understood that when the staple-pushing member 13 moves along the staple-pushing slot 116, it can directly or indirectly abut the anastomotic staple 4. Under the pushing action of the staple-pushing member 13, the anastomotic staple 4 can move towards the first side of the staple cartridge 11, thereby piercing and anastomosing the tissue pressed against the first side of the staple cartridge 11.

Figure 5:
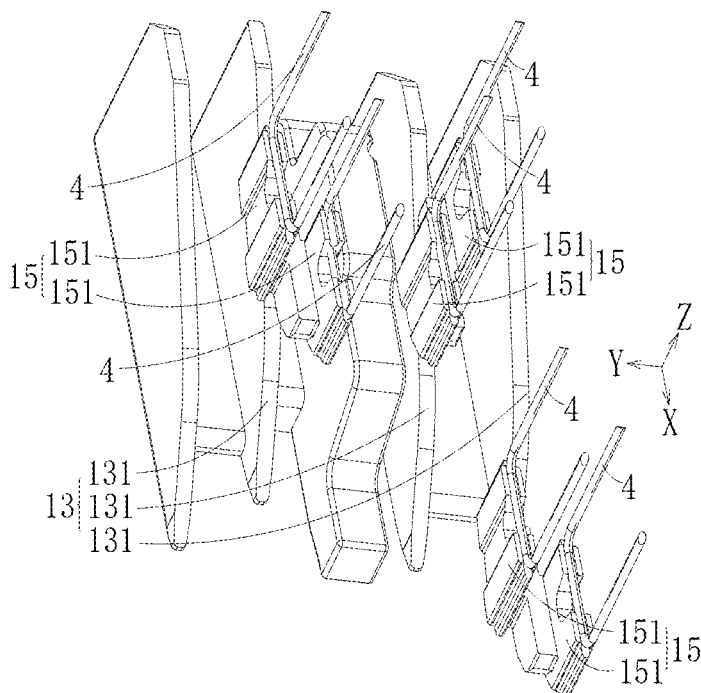
FIG. 5 is a schematic diagram showing a staple-pushing member in contact with multiple staple seats to achieve staple pushing in one embodiment of the present disclosure.
Figure 6:
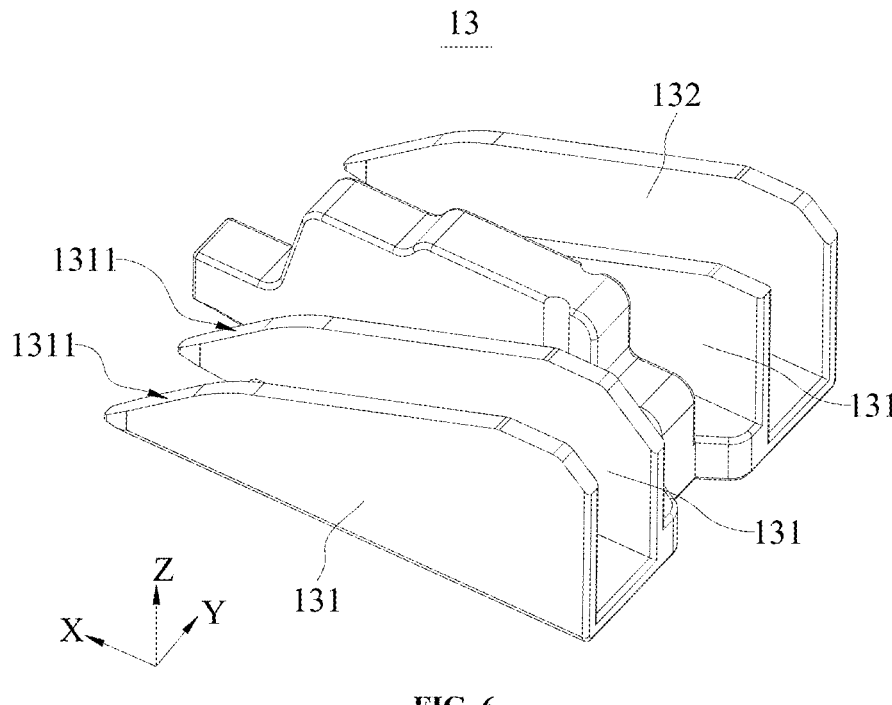
FIG. 6 is a structural schematic diagram of the staple-pushing member in one embodiment of the present disclosure.

FIG. 5 is a schematic diagram showing a staple-pushing member in contact with multiple staple seats to achieve staple-pushing in one embodiment of the present disclosure. FIG. 6 is a structural schematic diagram of the staple-pushing member in one embodiment of the present disclosure. As shown in FIGS. 2 to 6, optionally, the staple-pushing member 13 includes multiple staple-pushing plates 131 arranged at intervals in the slot-width direction of the feeding groove 113. The staple-pushing plates 131 and the staple-pushing slots 116 are provided in same number and inserted into the staple-pushing slots 116 in a one-to-one correspondence. In the embodiment, one side of the feeding groove 113 in the slot-width direction is provided with one staple-pushing slot 116, and the other side is provided with two staple-pushing slots 116. Therefore, three staple-pushing plates 131 are provided accordingly. The anastomotic staples 4 are slidably mounted in the staple slots 1141 through the staple seats 15 in the up-and-down direction. The staple-pushing plates 131 move in a staple-pushing direction (e.g., the positive direction of the X-axis in the figure) so as to push the staple seats 15 upward to trigger, thus enabling the anastomotic staples 4 to pierce out from the first side of the staple cartridge 11.

In the embodiment of the present disclosure, the staple seat 15 is accommodated in the staple slot 1141 and the staple-pushing slot 116, and the staple seat 15 is configured to support the anastomotic staple 4. Exemplarily, at least a portion of the staple seat 15 (e.g., each staple seat 15) includes two connected sub staple seats 151, wherein the two sub staple seats 151 are distributed roughly along the slot-width direction of the feeding groove 113. The two sub staple seats 151 are respectively in sliding fit with the staple slots 1141 in the two adjacent staple slot groups 114, thus allowing the staple seat 15 to move relative to the staple cartridge 11 in the second predetermined direction (the Z-axis direction shown in the figure, i.e., the up-and-down direction). Two anastomotic staples 4 are respectively arranged at the ends of the two sub staple seats 151 near the first side of the staple cartridge 11. In other words, one anastomotic staple 4 is mounted at the upward-facing end of each sub staple seat 151, and the two sub staple seats 151 are slidably mounted in the staple slots 1141 of different staple slot groups 114 in the up-and-down direction. It can be understood that the staple seat 15 spans between two different staple slot groups 114, with the middle part located in the staple-pushing slot 116, so that when the staple-pushing plate 131 moves in the staple-pushing slot 116, it can push the entire staple seat 15 to move in the second predetermined direction. Optionally, the staple seat 15 can be integrally molded or assembled from two sub staple seats 151.

Optionally, one end of the staple-pushing plate 131 in the first predetermined direction is provided with a guide surface 1311, wherein the guide surface 1311 is inclined relative to the first predetermined direction and inclined towards the second side of the staple cartridge 11. The guide surface 1311 is configured to push the anastomotic staples 4 to move toward the first side of the staple cartridge 11 when moving along the first predetermined direction. When the cutting knife drives the staple-pushing member 13 to move from back to front, the guide surface 1311 of the staple-pushing plate 131 is enabled to contact the bottom of the staple seat 15. As the staple-pushing plate 131 continues to move in the first predetermined direction, the staple seat 15 is restricted by the staple slot 1141 and cannot move in the first predetermined direction, resulting in relative sliding between the guide surface 1311 and the staple seat 15. The staple seat 15 is forced to move towards the first side of the staple cartridge 11 in the second predetermined direction, thereby pushing the staple seat 15 to slide upwards relative to the staple cartridge 11 and realizing the trigger of the anastomotic staples 4.

Optionally, one end of the staple-pushing slot 116 is provided with a second open port 1161, wherein the second open port 1161 is configured for the staple-pushing member 13 to pass through along the first predetermined direction. Optionally, a part of the staple-pushing member 13 can enter the staple-pushing slot 116 from the second open port 1161 in the first predetermined direction. In the embodiment, the second open port 1161 and the first open port 1131 are located at the same end of the staple cartridge 11.

Optionally, the staple-pushing member 13 further includes a guide part 132. The second side of the staple cartridge 11 is provided with a guide slot 117 extending along the first predetermined direction, wherein the guide slot 117 is in a sliding fit with the guide part 132 of the staple-pushing member 13. The cooperation of the guide part 132 and the guide slot 117 allows the staple-pushing member 13 to move more stably relative to the staple cartridge 11. Optionally, the guide part 132 is plate-shaped, and the guide part 132 is parallel to and arranged at intervals with each of the staple-pushing plates 131. The guide part 132 is provided on one side of multiple staple-pushing plates

131 in the slot-width direction of the feeding groove 113. Optionally, the guide part 132 is located on the side of the feeding groove 113 with fewer staple slot groups 114, which further balances the stability of the cooperation between the staple-pushing member 13 and the staple cartridge 11 on both sides in the slot-width direction.

Figure 7:
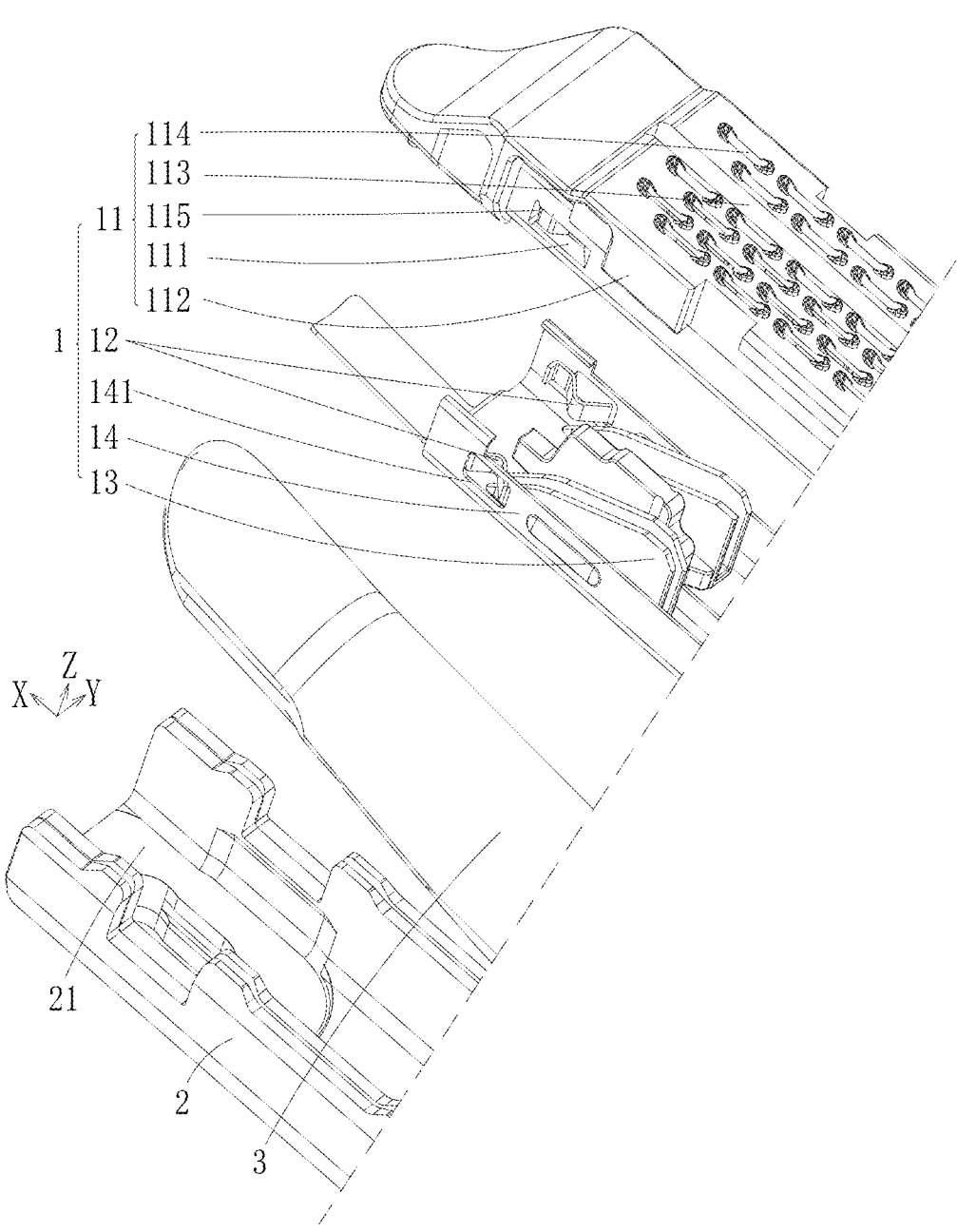
FIG. 7 is a structural schematic diagram of the staple cartridge assembly 1 further including an elastic limiting unit 12 in one embodiment of the present disclosure.
Figure 8:
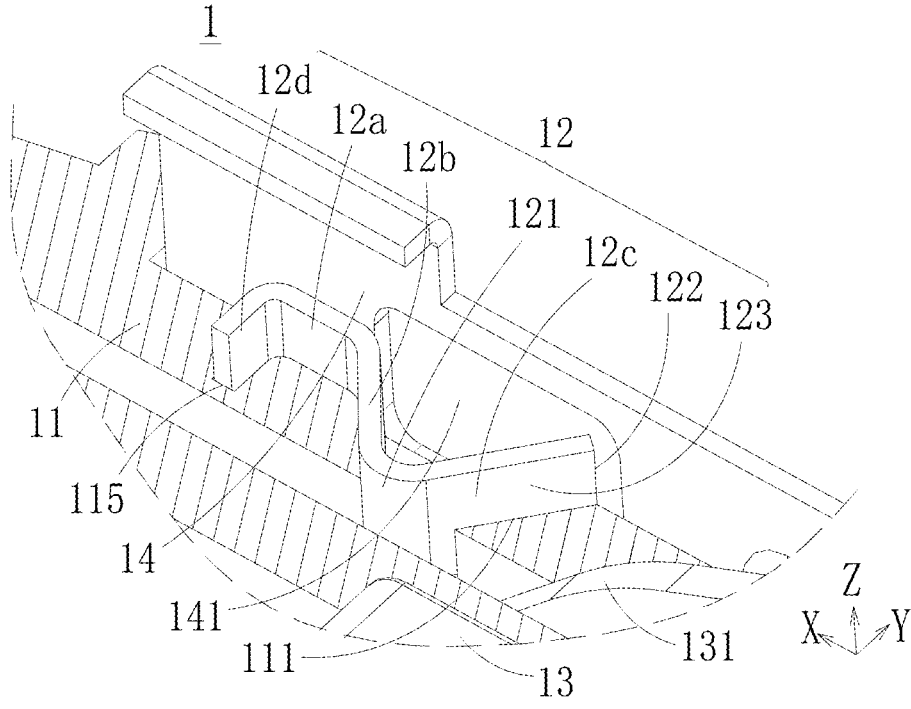
FIG. 8 is a schematic diagram of an arrangement of the elastic limiting unit in one embodiment of the present disclosure.

FIG. 7 is a structural schematic diagram of the staple cartridge assembly 1 further including an elastic limiting unit 12 in one embodiment of the present disclosure. FIG. 8 is a schematic diagram of an arrangement of the elastic limiting unit 12 in one embodiment of the present disclosure. As shown in FIGS. 7 and 8, optionally, the sliding direction of the staple-pushing member 13 is consistent with the extending direction of the feeding groove 113 of the staple cartridge 11. The staple cartridge assembly 1 further includes an elastic limiting unit 12, and the staple cartridge 11 is provided with a mounting hole 111, wherein the elastic limiting unit 12 is mounted at the mounting hole 111. The elastic limiting unit 12 includes an elastic force transfer structure 123, and a trigger part 121 and a limiting part 122 located at both ends of the elastic force transfer structure 123, wherein the trigger part 121 and the limiting part 122 are respectively arranged near an inner end and an outer end of the mounting hole 111. The trigger part 121 is arranged in a pushing movement path of the staple-pushing member 13 along the first predetermined direction. The elastic limiting unit 12 is configured to produce an elastic deformation when the trigger part 121 is pushed by the staple-pushing member 13, so that the trigger part 121 exits the pushing movement path. The elastic force transfer structure 123 is configured to apply an elastic driving force to the limiting part 121 for extending towards the outer end of the mounting hole 111 when the trigger part exits the pushing movement path.

In the embodiment, the limiting part 122 is arranged to correspond to a setting region of the outer surface of the staple cartridge 11. The setting region is the region of the outer surface of the staple cartridge 11 that opposes the staple cartridge base 2 after being assembled in the staple cartridge base 2. This ensures that in the state where the staple cartridge assembly 1 is assembled in the staple cartridge base 2, the limiting part 121, driven by the elastic force transfer structure 123 to extend towards the outer end of the mounting hole 111, will abut the inner wall of the staple cartridge base 2. The elastic limiting unit 12 is in a compressed state, thereby storing elastic potential energy.

In the embodiment, the staple cartridge assembly 1 is mounted in the staple cartridge base 2. Optionally, the staple cartridge base 2 forms a slot structure 21, wherein the staple cartridge assembly 1 is mounted in the slot structure 21. The top end of the staple cartridge assembly 1 is at least exposed outside the slot structure 21, so that, subsequently, the anastomotic staple 4 can be pushed out from the top end of the staple cartridge assembly 1 to contact with the staple-abutting seat 3. Optionally, the setting region on the outer surface of the staple cartridge 11 is the region opposite the inner side wall of the slot structure 21. It can be understood that when the limiting part 121 is pushed by the staple-pushing member 13 and exits the pushing movement path, the staple cartridge base 2 will abut the limiting part 121, causing the elastic limiting unit 12 to be compressed in the slot-width direction of the feeding groove 113. After the anastomosis operation is completed, when the staple cartridge assembly 1 is removed from the slot structure 21, the staple cartridge base 2 releases the abutment limit on the limiting part 121, allowing the limiting part 121 to extend outward under the elastic driving force of the elastic force transfer structure 123. Thereafter, the staple cartridge assembly 1 cannot be reassembled into the slot structure 21 of the staple cartridge base 2 due to the limiting effect of the limiting part 121.

In the embodiment, the staple cartridge assembly 1 further includes a staple cartridge cover 14, wherein the staple cartridge cover 14 is located on the back side of the staple cartridge 11 and is detachably connected to the staple cartridge 11. The staple cartridge assembly 1 is connected to the staple cartridge base 2 through the staple cartridge cover 14. Optionally, the staple cartridge cover 14 forms a holding space, and the staple cartridge 11 is arranged within the holding space of the staple cartridge cover 14.

A portion of the staple-pushing member 13 is located between the staple cartridge cover 14 and the staple cartridge 11. The staple cartridge cover 14 and the staple cartridge 11 together achieve the sliding and guiding of the staple-pushing member 13 in the first predetermined direction. The staple-pushing direction of the staple-pushing member 13 is from back to front. Specifically, when the anastomosis device is inserted into the preset position, and the staple-abutting seat 3 and the staple cartridge base 2 are closed to compress the tissue to be sutured, the staple-pushing member 13 moves from back to front under the driving action, for example, under the pushing action of the cutting knife. This drives the anastomotic staples 4 to be sequentially triggered from back to front, for example, triggered upwards. The triggered anastomotic staples 4 strike the forming slot 31 on the staple-abutting seat 3, so that the anastomotic staples 4 complete the suture by deformation. For instance, the anastomotic staple 4 deforms into a B-shape upon contacting the forming slot 31, which can meet the anastomotic requirements.

Figure 9:
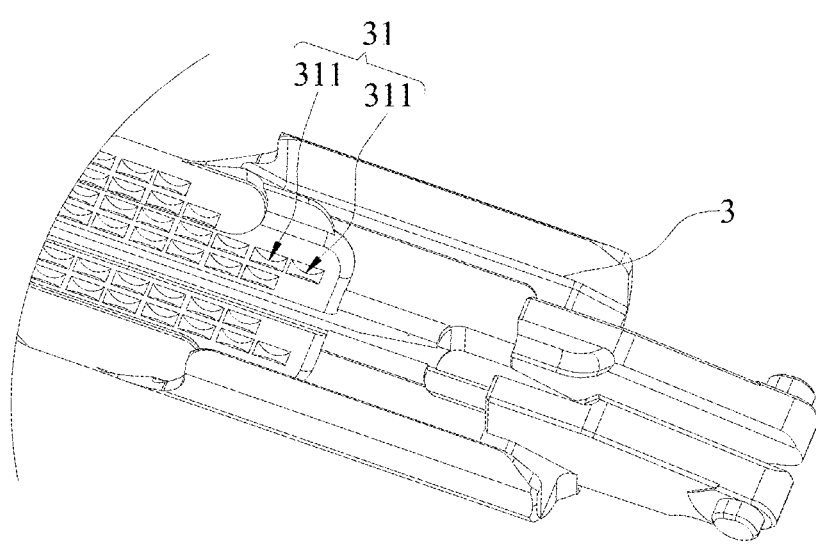
FIG. 9 is a partially schematic diagram of the staple-abutting seat in one embodiment of the present disclosure.

FIG. 9 is a partial schematic diagram of the staple-abutting seat in one embodiment of the present disclosure. As shown in FIG. 9, the side of the staple-abutting seat 3 facing the staple cartridge assembly 1 is provided with multiple forming slots 31. The number of forming slots 31 is the same as the number of staple slots 1141 on the staple cartridge. When the staple-abutting seat 3 is snapped, the multiple forming slots 31 align with the multiple staple slots 1141 in the second predetermined direction. Since the anastomotic staple 4 is provided with two sharp ends, each forming slot 31 is provided with a pair of grooves 311, which allows the two sharp ends of the anastomotic staple 4 to be bent and deformed in a direction close to each other when pressed into the two grooves 311 respectively, thus ultimately deforming the anastomotic staple 4 into a shape of letter "B".

It should be noted that when the staple-pushing member 13 is in its initial limit position, i.e., at the rear end of the staple cartridge 11, for example, in the case where the staple cartridge 11 of the staple cartridge assembly 1 is fully loaded with the anastomotic staples 4, the staple-pushing member 13 does not contact the trigger part 121. Therefore, the trigger part 121 remains in the movement path of the staple-pushing member 13 along its staple-pushing motion, and the limiting part 122 will not move outside the staple cartridge 11 due to the action of the staple-pushing member 13 on the trigger part 121. Optionally, when the trigger part 121 is not acted upon by the staple-pushing member 13, the limiting part 122 does not contact the staple cartridge base 2, such as not contacting the inner wall surface of the slot structure 21 of the staple cartridge base 2, and the staple cartridge assembly 1 can be smoothly inserted into the slot structure 21 of the staple cartridge base 2.

In the summary, to illustrate the content in the present disclosure by example, in which the mounting hole 111 is located on the first side wall 112 of the staple cartridge 11, the first side wall 112 is the side plate of the staple cartridge 11 in the width direction, i.e., the slot-width direction of the feeding groove 113. It should be understood that this is not limiting; for example, the mounting hole 111 can also be arranged on the bottom plate of the staple cartridge 11, which will not be detailed here.

The trigger part 121 of the elastic limiting unit 12 is arranged close to the inner end of the mounting hole 111. For example, the trigger part 121 of the elastic limiting unit 12 is located on the side of the inner end face of the mounting hole 111 away from the outer end face and is located in the movement path of the staple-pushing member 13 along its staple-pushing direction, where the staple-pushing direction is defined as a movement from back to front.

The limiting part 122 of the elastic limiting unit 12 is arranged close to the outer end of the mounting hole 111. For example, the limiting part 122 of the elastic limiting unit 12 is located on the side of the outer end face of the mounting hole 111 close to the inner end face, and the limiting part 122 corresponds to the setting region on the outer surface of the staple cartridge 11. The setting region is the region of the outer surface of the staple cartridge 11 configured to face the staple cartridge base 2, which is, for example, arranged opposite to the inner wall of the slot structure 21 on the staple cartridge base 2 configured to mount the staple cartridge assembly 1.

The specific structure of the elastic limiting unit 12 is not limited, as long as it is provided with an elastic force transfer structure 123, and a trigger part 121 and a limiting part 122 located at both ends of the elastic force transfer structure 123. The elastic force transfer structure 123 is configured to transmit elastic force between the trigger part 121 and the limiting part 122. For example, when an optional first one of the limiting part 122 and the trigger part 121 is unblocked in the left-right direction, and a second one of the limiting part 122 and the trigger part 121 is pressed in the left-right direction, the elastic force transfer structure 123 can enable the second one of the limiting part 122 and the trigger part 121 to move together. When the optional first one of the limiting part 122 and the trigger part 121 is blocked in the left-right direction, and the second one of the limiting part 122 and the trigger part 121 is pressed in the left-right direction, the potential energy of the elastic force transfer structure 123 increases, thus satisfying the requirement of reducing the distance that the limiting part 122 and the trigger part 121 are pressed in the left-right direction.

With this arrangement, the sliding direction of the staple-pushing member 13 is consistent with the extending direction of the feeding groove 113 of the staple cartridge 11. The staple cartridge 11 is provided with a mounting hole 111, wherein the elastic limiting unit 12 is mounted at the mounting hole 111 so as to realize the mounting of the elastic limiting unit 12 in the staple cartridge 11. The elastic limiting unit 12 includes an elastic force transfer structure 123, and a trigger part 121 and a limiting part 122 located at both ends of the elastic force transfer structure 123, wherein the trigger part 121 and the limiting part 122 are respectively arranged near an inner end and an outer end of the mounting hole 111. When the staple cartridge assembly 1 is mounted on the staple cartridge base 2 of the anastomosis device, since the limiting part 122 is arranged corresponding to a setting region of the outer surface of the staple cartridge 11, where the setting region is the region of the outer surface of the staple cartridge 11 configured to face the staple cartridge base 2, at least a portion of the anastomotic staples 4 in the staple cartridge 11 are triggered when the staple-pushing member 13 moves along its staple-pushing direction, for example, a movement from back to front, and contacts the trigger part 121. The trigger part 121, pushed by the staple-pushing member 13, moves outwardly from the staple cartridge 11. The elastic force transfer structure 123, acted upon by the trigger part 121, drives the limiting part 122 to move outwardly from the staple cartridge 11. Consequently, the limiting part 122 abuts the inner wall of the staple cartridge base 2, for example, the slot structure 21. At this moment, the potential energy of the elastic force transfer structure 123 is high, but it does not affect the normal use of the staple cartridge assembly 1 in the staple cartridge base 2, and the staple cartridge assembly 1 can be normally detached from the staple cartridge base 2. If the staple cartridge assembly 1 is removed from the staple cartridge base 2, the abutment between the staple cartridge base 2 and the limiting part 122 is released. Driven by the potential energy of the elastic force transfer structure 123, the limiting part 122 moves outwardly from the staple cartridge 11. This enlarges the size of the staple cartridge assembly 1 at the limiting part 122, which substantially forms an obstruction. Specifically, this forms the obstruction when the staple cartridge assembly 1 is reassembled into the staple cartridge base 2 in this state. In other words, the difficulty in which at least a portion of the anastomotic staples 4 is loaded by the triggered staple cartridge assembly 1 into the staple cartridge base 2 is greatly increased. Therefore, the misassembly of at least a portion of the anastomotic staples 4 by the triggered staple cartridge assembly 1 can be prevented to a certain extent.

As shown in FIGS. 7 and 8, optionally, the staple cartridge 11 is provided with the trigger part 121 corresponding to a terminal limiting position of the pushing movement path of the staple-pushing member 13.

In the embodiment, the staple cartridge assembly 1 includes only one elastic limiting unit 12, and the elastic limiting unit 12 includes only one trigger part 121 and one limiting part 122. In this case, the position of the mounting hole 111 corresponds to the terminal limit position of the staple-pushing member 13. The following description will use this as an example to illustrate the present disclosure.

However, it should be understood that this is not limiting. For instance, multiple mounting holes 111 can be provided, and multiple elastic limiting units 12 can be provided correspondingly. Alternatively, the elastic limiting unit 12 can include multiple trigger parts 121 along with their corresponding elastic force transfer structures 123 and limiting parts 122. In this case, when the staple-pushing member 13 completes the pushing of different quantities of anastomotic staples 4 and is positioned differently, the corresponding trigger parts 121 can be activated to prevent misassembly of the staple cartridge assembly 1 after detaching the staple cartridge assembly 1. This can be configured according to actual needs and will not be described in detail here.

It should be understood that the terminal limiting position refers to the position where the staple-pushing member 13 is at the foremost end of the staple cartridge 11. When the staple-pushing member 13 is at the terminal limiting position, all the anastomotic staples 4 within the staple cartridge 11 are in a triggered state, meaning that the staple cartridge 11 is empty. With this arrangement, when the staple cartridge assembly 1 is detached from the staple cartridge base 2, the limiting part 122 of the elastic limiting unit 12 can protectively prevent the misassembly of the empty staple cartridge assembly 1, thus avoiding the undesirable consequences due to assembling the empty staple cartridge assembly 1 to the staple cartridge base 2.

Optionally, the staple cartridge assembly 1 is configured to connect to the staple cartridge base 2 via a staple cartridge cover 14. The staple cartridge cover 14 is provided with a through hole 141. The through hole 141 communicates with the mounting hole 111, and the through hole 141 is configured to allow the passage of the limiting part 122.

Specifically, the staple cartridge cover 14 can be detachably connected to the staple cartridge 11, for example, through a snap-fit connection. The staple cartridge assembly 1 is connected to the slot structure 21 of the staple cartridge base 2 through the staple cartridge cover 14, for example, through a snap-fit connection. The specific connection methods of the two can utilize relevant technology, such as using related technology of the applicant of the present disclosure prior to the filing date, which will not be detailed here.

Therefore, it is possible to ensure, on the basis of the protection of the bottom of the staple cartridge 11 by the staple cartridge cover 14, that the limiting part 122 can smoothly move outwardly from the staple cartridge 11, for example, in the left-right direction, and abut the inner wall of the slot structure 21 of the staple cartridge base 2, or provide prevention against the misassembly of the empty staple cartridge assembly 1.

Optionally, the elastic limiting unit 12 is an elastic piece structure, wherein a fixed end of the elastic piece structure is fixedly arranged at an edge of the mounting hole 111, and the elastic force transfer structure 123, the trigger part 121, and the limiting part 122 are all formed on the elastic piece structure.

Specifically, the elastic piece structure can be formed from an elastic piece. In this case, the elastic force transfer structure 123, the trigger part 121, and the limiting part 122 are formed through the elastic piece structure, making the elastic limiting unit 12 simple in structure and highly reliable. In other embodiments, the elastic piece structure can also be formed by connecting multiple elastic pieces. This is not limited as long as it meets usage requirements.

As shown in FIG. 8, optionally, the elastic piece structure is bent to form a first section 12a, a second section 12b, and a third section 12c sequentially connected, wherein the first section 12a forms the fixed end of the elastic piece structure and is fixedly connected to staple cartridge 11 on the circumferential side of the mounting hole 111, and the second section 12b and the third section 12c are each provided in an inclined manner with respect to the first section 12a. The third section 12c and the second section 12b form an angle, and the opening direction of the angle formed by the second section 12b and the third section 12c is consistent with the depth direction of the mounting hole 111. The connection part of the second section 12b and the third section 12c forms the trigger part 121, and the third section 12c forms the elastic force transfer structure 123.

Exemplarily, the elastic piece structure is attached to the staple cartridge 11 in the first section 12a, thereby fixing the position of the fixed end of the elastic piece structure on the staple cartridge 11. The inner wall of the staple cartridge cover 14 and the outer wall of the staple cartridge 11 clamp the fixed end of the elastic piece structure. The limiting part 122 is arranged at one end of the third section 12c near the outer side of the mounting hole 111, and the trigger part 121 is arranged at the end of the third section 12c near the inner side of the mounting hole 111. The second section 12b is arranged in an inclined manner relative to the first section 12a.

Thus, after bending an elastic piece, an elastic limiting unit 12 can be formed, and there is no need to use multiple components to form the elastic limiting unit 12, whose structure is simple. The third section 12c is enabled to move as a whole with respect to the first section 12a, and the positional reset of the third section 12c is conducted by the second section 12b. For example, the end of the third section 12c near the second section 12b can perform resettable movement with respect to the first section 12a in the depth direction of the mounting hole 111, which is the left-right direction. The third section 12c is arranged in an inclined manner with respect to the first section 12a, which allows the trigger part 121 and the limiting part 122 of the third section 12c to move relatively and to some extent accumulate potential energy through the elastic deformation of the third section 12c. The relative positions of the trigger part 121 and the limiting part 122 can be reset through the deformation of the third section 12c itself, making the structure simple and practical.

As shown in FIG. 8, optionally, the first section 12a is connected to an insertion section 12d. The staple cartridge 11 is provided with a slot 115, and the insertion section 12d is inserted into the slot 115. Exemplarily, the insertion section is formed by bending the end of the first section 12a away from the second section 12b. The depth direction of the slot 115 can be consistent with the depth direction of the mounting hole 111.

Exemplarily, when the first section 12a is attached to the staple cartridge 11 on the outer end face of the mounting hole 111, the end of the first section 12a away from the second section 12b is bent inward towards the staple cartridge 11 to form the insertion section. With this arrangement, the connection reliability between the fixed end of the elastic piece structure and the staple cartridge 11 can be enhanced through the insertion connection of the insertion section 12d and the slot 115.

It should be understood that one or more of the trigger parts 121 and the limiting parts 122 can be arranged with guiding slopes configured for contact and guidance as needed. For example, one or more of the trigger parts 121 and the limiting parts 122 can be arranged as ball convex structures. This can prevent scratching and damage to the contact surface when the staple-pushing member 13 contacts the trigger part 121, and also prevent scratching and damage to the contact surface when the limiting part 122 contacts the staple cartridge base 2, thus extending the lifespan of the component and reducing noise and the likelihood of debris from scratches.

In the aforementioned embodiment, optionally, the staple cartridge base 2 is provided with a slot structure 21, and the staple cartridge assembly 1 can be arranged into the slot structure 21 along the first predetermined direction. The first section 12a, the second section 12b, and the third section 12c are connected sequentially along the first predetermined direction.

Optionally, the staple cartridge assembly 1 is configured to be arranged into the slot structure 21 by moving from front to back. The first section 12a, the second section 12b, and the third section 12c are sequentially distributed from front to back. At this time, the end of the third section 12c forms the limiting part 122, and the other end forms the trigger part 121. When the staple-pushing member 13 of the staple cartridge assembly 1 does not contact the trigger part 121 and the staple cartridge assembly 1 is in a disassembled state, if the staple cartridge assembly 1 needs to be moved from front to back and pushed into the slot structure 21, at this time, the limiting part 122 at the end of the third section

12c will extend beyond the outer surface of the staple cartridge assembly 1, for example, beyond the outer surface of the staple cartridge cover 14, along the left-right direction. The front end surface of the slot structure 21 of the staple cartridge base 2 will abut the limiting part 122. As the staple cartridge assembly 1 is pushed from front to back, the limiting part 122, subjected to a force, has a tendency to move forward with respect to the first section 12a, and has a tendency to move outwardly in an expansive manner, at least initially. This makes it more difficult to push the staple cartridge assembly 1 into the slot structure 21 from front to back, thus achieving better prevention against misassembly.

As shown in FIG. 8, in the aforementioned embodiment, optionally, the staple cartridge cover 14 presses the fixed end of the elastic piece structure against the end surface of the outer end of the mounting hole 111.

Specifically, the inner surface of the staple cartridge cover 14 in the left-right direction presses the first section 12a against the end surface of the outer end of the mounting hole 111 and keeps the insertion section 12d in an inserted state with the slot 115, thus ensuring the reliability of the connection between the elastic piece structure and the staple cartridge 11.

At this time, it should be understood that a holding groove can be provided at the end surface of the outer end of the mounting hole 111 in the staple cartridge 11, wherein the holding groove is configured to accommodate the elastic piece structure, such as accommodating the first section 12a.

As shown in FIG. 8, in the aforementioned embodiment, optionally, the first side walls 112 on both sides of the staple cartridge 11 along the width direction are provided with the mounting holes 111 and the elastic limiting units 12. Optionally, the two mounting holes 111 and the two elastic limiting units 12 are arranged in a symmetrical manner along the left-right direction. In this way, during the prevention against the misassembly, the left and right sides of the staple cartridge assembly 1 are obstructed by two limiting parts 122, thus making the forces more balanced and avoiding damage to the staple cartridge assembly 1 that might be caused by uneven forces on the left and right sides, thus ensuring higher reliability.

It should be understood that the structure of the elastic limiting unit 12 has been exemplarily described above, but it is not limited to this. For example, in another optional solution of the elastic piece structure, the end of the second section 12b away from the first section 12a can be connected between the two ends of the third section 12c, which will not be detailed here.

Figure 10:
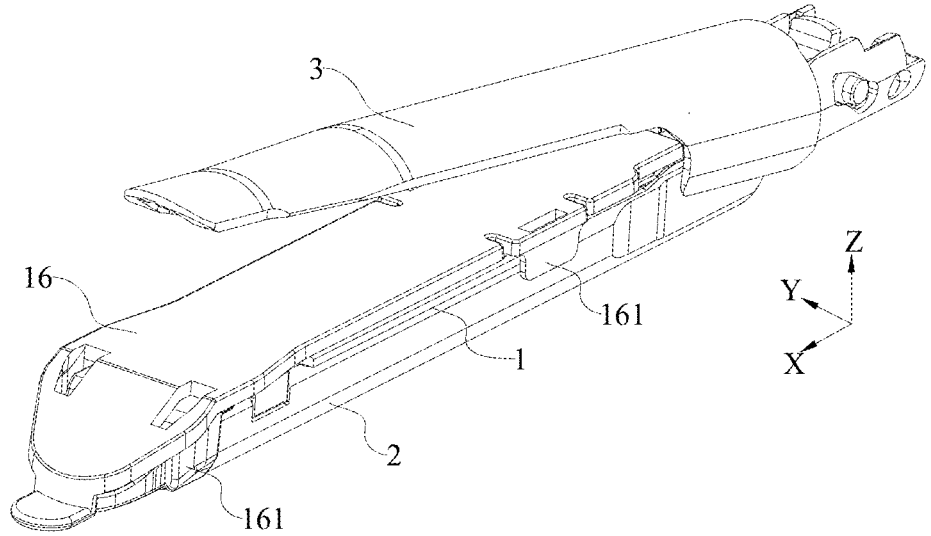
FIG. 10 is a schematic diagram of an assembly of a protective member of the staple cartridge assembly in one embodiment of the present disclosure.

FIG. 10 is a schematic diagram of an assembly of a protective member 16 of the staple cartridge assembly 1 in one embodiment of the present disclosure. As shown in FIG. 10, optionally, the staple cartridge assembly 1 also includes a protective member 16. Before the anastomosis operation, the protective member 16 covers the first side of the staple cartridge 11, thereby protecting the first side of the staple cartridge 11. For instance, the protective member 16 can prevent external foreign objects from entering the staple slots 1141 of the staple cartridge 11 and can also prevent the anastomotic staples 4 from falling out of the staple slots 1141. Optionally, the protective member 16 is provided with one or more snapping parts 161 in the left-right direction, wherein the snapping part 161 can be snapped with the staple cartridge 11 or the staple cartridge base 2, thereby making the protective member 16 less likely to fall off. When performing the anastomosis operation, the protective member 16 needs to be removed. It should be understood that the external force required to remove the protective member 16 should be greater than the snapping force of the snapping part 161. In other optional embodiments, the protective member 16 can also be fixed by other means. For example, it is affixed to the first side of the staple cartridge 11 using bonding. Before the anastomosis operation, the protective member 16 can be peeled off by applying an external force greater than the adhesive force.

In summary, compared to related prior art, the feeding groove of the staple cartridge provided in the embodiments of the present disclosure is arranged to extend in the first predetermined direction, and the feeding groove is configured for the cutting knife to pass through. When the staple cartridge is applied to the anastomosis device, specifically, when the anastomosis device compresses the tissue to be operated on through the staple-abutting seat and the staple cartridge, the cutting knife can perform cutting operations by moving through the feeding groove. At the same time, multiple staple slot groups are distributed on both sides of the feeding groove along the slot-width direction of the feeding groove, and the number of staple slot groups on both sides of the feeding groove is different, thereby making the stability of the anastomosis and the width of the anastomosis on both sides of the feeding groove different along the slot-width direction. This can specifically enhance the stability of the anastomosis on the side with a greater number of staple slot groups and can meet the differentiated anastomotic requirements of the tissue retention end and the tissue removal end. Specifically, the side with a greater number of staple slot groups corresponds to the tissue retention end, and the side with fewer staple slot groups corresponds to the tissue removal end, which can meet the anastomotic requirements of the tissue retention end, improve the anastomosis effect on the tissue retention end, and reduce the amount of bleeding on the tissue retention end. Simultaneously, it can also prevent over-functioning anastomosis on the tissue removal end due to too many anastomotic staples, thus avoiding the waste of anastomotic staples. Overall, the staple cartridge in the embodiments of the present disclosure is beneficial for improving the utilization rate of anastomotic staples, reducing the amount of bleeding on the tissue retention end, and enhancing the anastomosis effect on the tissue retention end.

In the description of the summary, reference terms such as "an embodiment", "some embodiments", "an example", "specific examples", or "some examples" in the description refer to one or more embodiments or examples of the present disclosure that include specific features, structures, materials, or characteristics described in conjunction with that embodiment or example. In the summary, illustrative expressions of the above terms do not necessarily have to refer to the same embodiments or examples. Moreover, specific features, structures, materials, or characteristics described can be appropriately combined in any one or more embodiments or examples. Additionally, in a non-conflicting manner, those skilled in the art may combine and modify different embodiments or examples and the features of the different embodiments or examples as described in the summary.

While exemplary embodiments of the present disclosure have been shown and described above, it should be understood that these embodiments are illustrative and should not be construed as limiting the scope of the present disclosure. Those skilled in the art can make variations, modifications, substitutions, and alterations to the above embodiments within the scope of the present disclosure.

INDUSTRIAL PRACTICALITY

In summary, the present disclosure provides a staple cartridge, a staple cartridge assembly, and an anastomosis device, which is beneficial for improving the utilization rate of anastomotic staples, reducing the amount of bleeding on the tissue retention end, and enhancing the anastomosis effect on the tissue retention end.

What is claimed is:

1. A staple cartridge assembly, comprising a staple-pushing member and a staple cartridge, wherein the staple cartridge is provided with a feeding groove and multiple staple slot groups; the feeding groove is arranged to extend in a first predetermined direction, and the feeding groove is configured for a cutting knife to pass through; each of the staple slot groups comprises multiple staple slots distributed along the first predetermined direction, wherein the staple slots are configured for mounting anastomotic staples; the multiple staple slot groups are arranged at intervals in a slot-width direction of the feeding groove; at least one staple slot group is distributed on both sides of the feeding groove in the slot-width direction; and numbers of the staple slot groups on both sides of the feeding groove in the slot-width direction are different;

wherein the staple-pushing member is configured to move relative to the staple cartridge so as to trigger the anastomotic staples in the staple slots of the staple cartridge, wherein the staple-pushing member is configured to move relative to the staple cartridge in the first predetermined direction; the staple cartridge assembly further comprises an elastic limiting unit, and the staple cartridge is provided with a mounting hole, wherein the elastic limiting unit is mounted at the mounting hole; the elastic limiting unit comprises an elastic force transfer structure, and a trigger part and a limiting part located at both ends of the elastic force transfer structure, wherein the trigger part and the limiting part are respectively arranged near an inner end and an outer end of the mounting hole; the trigger part is arranged in a pushing movement path of the staple-pushing member in the first predetermined direction; the elastic limiting unit is configured to produce an elastic deformation when the trigger part is pushed by the staple-pushing member so that the trigger part exits the pushing movement path; and the elastic force transfer structure is configured to apply an elastic driving force to the limiting part to extend towards an outer end of the mounting hole when the trigger part exits the pushing movement path.

2. The staple cartridge assembly according to claim 1, wherein the feeding groove and the staple slots penetrate the staple cartridge along a second predetermined direction, and the second predetermined direction is perpendicular to the first predetermined direction and the slot-width direction; the staple cartridge is provided with a first side and a second side that are opposite in the second predetermined direction; an opening of the staple slots formed on the first side of the staple cartridge is configured for a front end of a triggered anastomotic staple to extend out, and the second side of the staple cartridge is provided with multiple staple-pushing slots extending in the first predetermined direction; the staple-pushing slots are arranged between two adjacent staple slot groups on a same side of the feeding groove, and the staple-pushing slots communicate with the staple slots of two adjacent staple slot groups in the slot-width direction; and the staple-pushing member is arranged on the second side of the staple cartridge; at least a portion of the staple-pushing member extends into the staple-pushing slots and can move along the staple-pushing slots, so as to push the anastomotic staples located in the staple slots to move toward the first side of the staple cartridge.

3. The staple cartridge assembly according to claim 2, wherein the staple-pushing member comprises multiple staple-pushing plates, the multiple staple-pushing plates are arranged at intervals in the slot-width direction, and the staple-pushing plates and the staple-pushing slots are provided in same number and inserted into the staple-pushing slots in a one-to-one correspondence.

4. The staple cartridge assembly according to claim 3, wherein one end of the staple-pushing plates in the first predetermined direction is provided with a guide surface, the guide surface is inclined relative to the first predetermined direction and inclined towards the second side of the staple cartridge, and the guide surface is configured to push the anastomotic staples to move toward the first side of the staple cartridge when moving along the first predetermined direction.

5. The staple cartridge assembly according to claim 2, wherein the second side of the staple cartridge is provided with a guide slot extending in the first predetermined direction; and the staple-pushing member further comprises a guide part, wherein the guide slot is in a sliding fit with the guide part of the staple-pushing member.

6. The staple cartridge assembly according to claim 2, wherein the staple cartridge assembly further comprises staple seats and the anastomotic staples, and the staple seats are housed in the staple slots and the staple-pushing slots; each of the staple seats comprises two connected sub staple seats, wherein the two sub staple seats are respectively in a sliding fit with the staple slots in two adjacent staple slot groups so that the staple seats can move relative to the staple cartridge in the second predetermined direction; and each sub staple seat is provided with one anastomotic staple at an end near the first side of the staple cartridge.

7. The staple cartridge assembly according to claim 1, wherein the staple cartridge is provided with the trigger part corresponding to a terminal limiting position of the pushing movement path of the staple-pushing member;

and/or the elastic limiting unit is an elastic piece structure, wherein a fixed end of the elastic piece structure is fixedly arranged at an edge of the mounting hole, and the elastic force transfer structure, the trigger part, and the limiting part are all formed on the elastic piece structure.

8. The staple cartridge assembly according to claim 7, wherein the elastic piece structure is bent to form a first section, a second section, and a third section sequentially connected; the first section forms the fixed end of the elastic piece structure and is fixedly connected to the staple cartridge, and the second section and the third section are each provided in an inclined manner with respect to the first section; the third section and the second section form an angle, wherein an opening direction of the angle formed by the second section and the third section is consistent with a depth direction of the mounting hole; and a connection part of the second section and the third section forms the trigger part, and the third section forms the elastic force transfer structure.

9. The staple cartridge assembly according to claim 7, wherein the staple cartridge assembly further comprises a staple cartridge cover, and the staple cartridge cover is detachably connected to the staple cartridge; the staple cartridge cover forms a holding space, wherein the staple cartridge is arranged in the holding space of the staple cartridge cover; the staple cartridge cover is provided with a through hole, wherein the through hole communicates with the mounting hole, and the through hole is configured for the limiting part to pass through; and an inner wall of the staple cartridge cover and an outer wall of the staple cartridge clamp the fixed end of the elastic piece structure.

10. An anastomosis device, comprising the staple cartridge assembly according to claim 1.

11. The staple cartridge assembly according to claim 1, wherein the feeding groove is arranged to extend in a straight line; one end of the feeding groove is provided with a first open port, wherein the first open port is configured for the cutting knife to enter the feeding groove along the first predetermined direction.

12. The staple cartridge assembly according to claim 1, wherein the multiple staple slot groups on a same side of the feeding groove are distributed at equal intervals.

13. The staple cartridge assembly according to claim 1, wherein the staple slots of two adjacent staple slot groups on a same side of the feeding groove are distributed in a staggered manner.

14. The staple cartridge assembly according to claim 1, wherein two or more staple slot groups are provided on either side of the feeding groove along the slot-width direction.

15. The staple cartridge assembly according to claim 1, wherein a difference in the numbers of the staple slot groups on both sides of the feeding groove along the slot-width direction is less than or equal to two.

* * * * *